United States Patent
McKenzie

Patent Number: 5,224,501
Date of Patent: Jul. 6, 1993

[54] TOOTH-FLOSSING DEVICE

[76] Inventor: Clancy D. McKenzie, P.O. Box 345, Bala-Cynwyd, Pa. 19004

[21] Appl. No.: 875,566

[22] Filed: Apr. 27, 1992

Related U.S. Application Data

[63] Continuation of Ser. No. 700,817, May 16, 1991, abandoned.

[51] Int. Cl.$^5$ .............................................. A61C 15/00
[52] U.S. Cl. ..................................... 132/323; 132/321
[58] Field of Search ................ 132/321, 323, 327, 329

[56] References Cited

U.S. PATENT DOCUMENTS

| | | | |
|---|---|---|---|
| 1,559,320 | 10/1925 | Hirsh | 132/323 |
| 3,393,687 | 7/1968 | Whitman | 132/323 |
| 4,050,470 | 9/1977 | Miller | 132/323 |
| 4,403,625 | 9/1983 | Sanders et al. | 132/323 |
| 4,638,824 | 1/1987 | De La Hoz | 132/323 |
| 4,926,820 | 5/1990 | Wearn | 132/323 |
| 4,974,614 | 12/1990 | Selker | 132/321 |
| 5,086,792 | 2/1992 | Chodorow | 132/323 |

Primary Examiner—Gene Mancene
Assistant Examiner—Jeffrey A. Smith
Attorney, Agent, or Firm—Eugene Chovanes

[57] ABSTRACT

An improved device for holding and manipulating dental floss for the removal of food particles, tartar and plaque from the teeth is described in which a loop of dental floss is connected between a pair of separate handles; the loop of dental floss being long enough to permit lateral motion across the tooth surface. The devices are either disposable or sterilizable for reuse.

3 Claims, 2 Drawing Sheets

TOOTH-FLOSSING DEVICE

This is a continuation of copending application Ser. No. 07/700,817 filed on May 16, 1991 now abandoned.

FIELD OF THE INVENTION

The present invention relates to the field of personal hygiene and, more particularly, to dental hygiene and specifically to an improved device for flossing the teeth.

BACKGROUND OF THE INVENTION

It has long been known in the field of dental hygiene that it is important to remove food particles, tartar, and plaque, preferably after each meal, but at least once or twice a day. The removal of such dental contaminants is accomplished by various means such as by brushing, water spray and the like; one of the most effective means being by the use of dental floss. Dental floss is generally held in the hands and manipulated by the fingers; the floss being inserted between two adjacent teeth or looped partially around a single tooth and reciprocated back and forth against the tooth to remove the food particles, tartar and plaque. This procedure requires a certain amount of manual dexterity and may be difficult for persons whose fingers are missing, malformed or arthritic.

THE PRIOR ART

A variety of devices have been suggested in the prior art to facilitate the manipulation of dental floss. Among these are devices consisting of a bifurcated or forked handle. In some of these devices, a very short length of dental floss is stretched tautly transversely between the two tines of the forked handle; the spacing between the tines and, therefore, the length of operable dental floss being only about twice the width of a large tooth. In use, such a device is manipulated so as to draw the dental floss up and down against the surface of the tooth to be cleaned. Due to the short span of the dental floss, only very limited side-to-side or lateral action is possible. In another device of the prior art, the dental floss is stretched tautly between the two tines of a new-moon-shaped bifurcated head mounted at an angle on a single handle. These devices may provide a slightly longer taut span of dental floss than those mentioned above, but the length of floss is still too short to provide good lateral movement across the tooth. Moreover, since the floss is stretched in a straight line in both of these devices, it can not be looped around a tooth to clean in an arc of 180° but can only be applied against a much lesser arc of the tooth surface.

It is apparent from the foregoing that a need has existed in the art for a device to facilitate the handling of dental floss which is easy to use by anyone having even limited use of their hands and which also permits the fullest practical contact of the dental floss with the tooth.

It is an object of the present invention, therefore, to provide a device for the handling of dental floss which is not only easy to manipulate but which also provides a loop of dental floss long enough to permit lateral and wide arc cleaning of the tooth surface.

It is another object of the invention to provide a simple device for handling a loop of dental floss.

It is still another object of the invention to provide an inexpensive device for handling a loop of dental floss which can be discarded after use.

It is yet another object of the invention to provide a device for handling a loop of dental floss which can be sterilized for re-use and in which the loop of dental floss is replaceable.

SUMMARY OF THE INVENTION

The foregoing and other objects of the present invention, which will become apparent below, are achieved by providing a dental floss manipulating device comprising a pair of separate handles connected by a loop of dental floss. The device may be so inexpensive as to be disposable after a single use or use over a short period of time. Devices of the same structure can also be provided which are capable of sterilization for continued reuse and, if desired, in which the loop of dental floss is replaceable.

DETAILED DESCRIPTION OF THE INVENTION

The invention will now be described in greater detail in conjunction with the accompanying drawings, in which.

Figure 1:
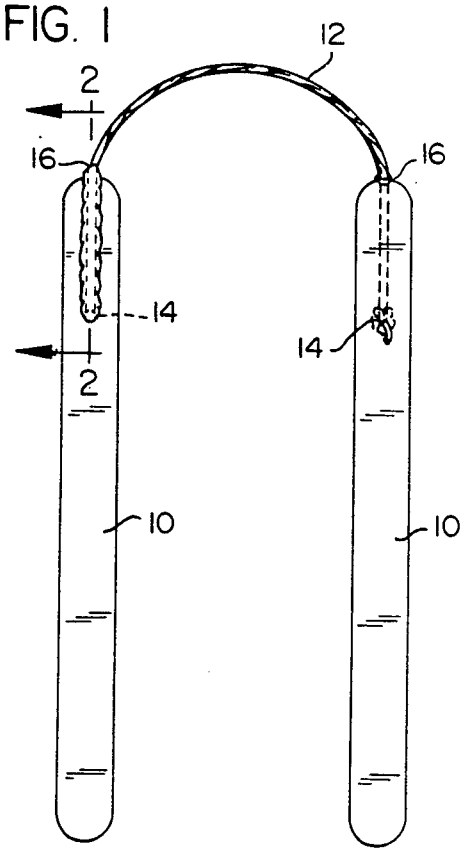
FIG. 1 is a slightly enlarged plan view of a typical embodiment of the invention.
Figure 2:
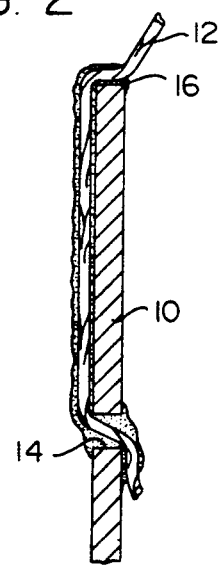
FIG. 2 is an enlarged fragmentary sectional view taken on the line 2,2 of FIG. 1, showing how the terminal ends of the dental floss loop are fastened to the handles.

Referring now to the drawings, a typical disposable embodiment of the invention is shown in FIGS. 1 and 2. In this dental floss manipulating device, a pair of separate handles 10 are connected by a strand or loop of dental floss 12; one end of the loop being attached to one handle 10 and the other end being attached to the other handle 10. The handles 10 are of a size and shape to be easily gripped and held by the fingers; preferably one in each hand. The handles may be composed of any relatively stiff suitable material such as wood, metal, plastic, stiffened paper and the like; an especially suitable and inexpensive example being the thin, narrow wooden sticks used for frozen confections such as popsicles and ice cream bars. The dental floss may be attached to the handles in any suitable manner. In the embodiment shown in FIGS. 1 and 2, terminal ends of the loop of dental floss 12 are passed through a hole 14 in each handle 10 and led up one surface of the handle to pass over the upper terminal ends of the handles and from there to the other handle 10. Each end of the floss loop 12 is glued or otherwise fastened to the surface of a handle 10. The glue may also be applied in the hole 14 and opposite side of the handle to anchor the floss. It is important that the floss loop be firmly glued to the handles 10 at the points 16 in the embodiment of FIGS. 1 and 2. The device shown in FIGS. 1 and 2 is so inexpensive to manufacture that it may be discarded after only a few uses or, indeed, after a single use. These devices may be supplied in a sterile package containing any suitable number or a single device.

Figure 3:
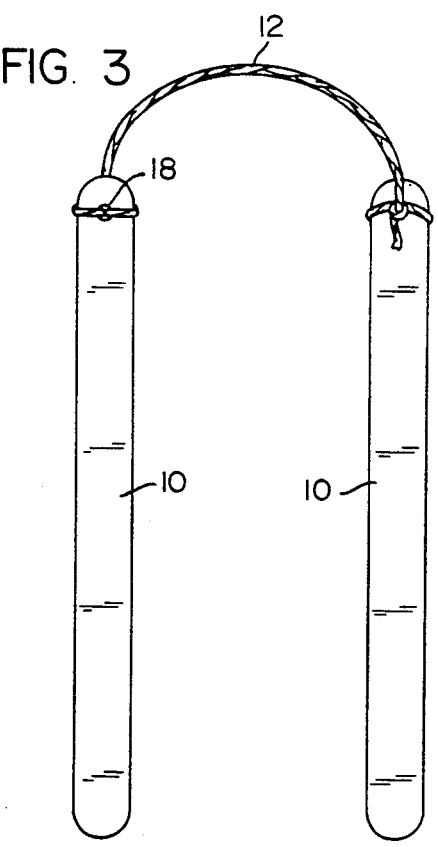
FIG. 3 is a plan view of a second embodiment of the invention in which the dental floss is replaceable.
Figure 4A:
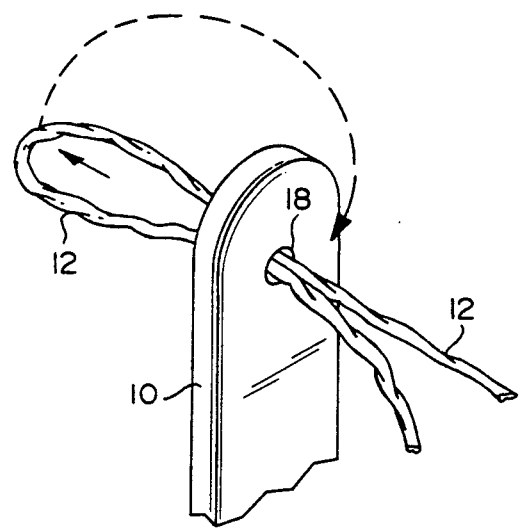
FIGS. 4A and 4B are enlarged fragmentary isometric views of the upper terminal end of a handle showing sequentially one means of attaching the dental floss.
Figure 4B:
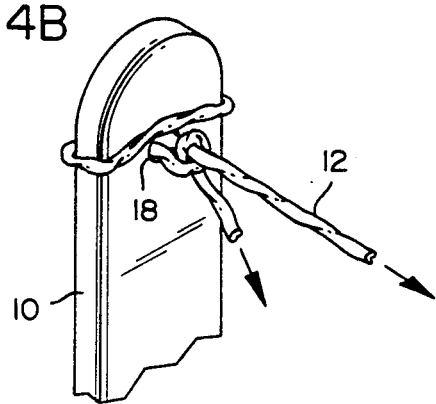

Another embodiment of the invention, shown in FIGS. 3 and 4, is intended to permit replacement of the dental floss. The handles 10 are provided with holes 18 in their upper ends to receive the dental floss 12. The holes 18 may be round as shown or may have any other suitable configuration such as slots, or ovals, or other shapes. The dental floss 12 is connected to the handles 10 by passing it through the holes 18 and fastening it to the handle in any convenient manner. This may be by means of any suitable knot or hitch; one simple and efficient manner is to loop the floss to the handle by forming a bight in one end of a strand of floss, inserting the bight through the hole 18 and then leading the inserted bight over the end of the handle 10 and pulling the loop tight. The short, loose end of the bight may, if desired, be fastened to the running end by one or more half-hitches for added security. The running end of the dental floss is then connected to the other handle in a similar fashion; all as shown in FIGS. 3 and 4.

The handles 10 in the embodiment shown in FIGS. 3 and 4 may be made of wood or the like as in the device of FIGS. 1 and 2, but are preferably made of a plastic material capable of being sterilized for reuse. Sterilization may be by the use of heat or steam in professional use or by use of a sterilizing fluid in the home. For example, the device may be immersed in water to which a tablet is added which foams to clean and sterilize dentures.

Figure 5:
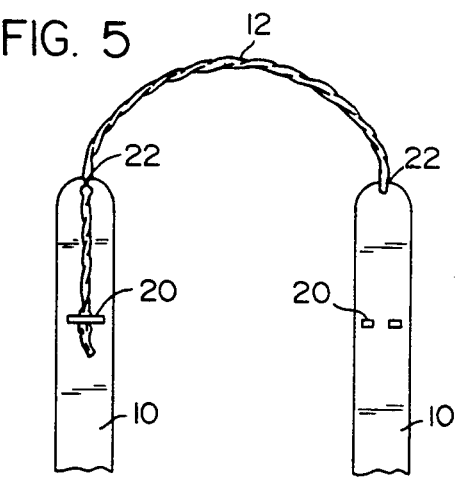
FIG. 5 is a fragmentary plan view showing another embodiment of the invention wherein a combination of slots and staples are used to secure the terminal ends of the dental floss to the handles.

Still another embodiment of the invention is shown in FIG. 5 in which the floss 12 is fastened to the handles 10 by mechanical means such as staples 20 and led over notches 22.

Figure 6:
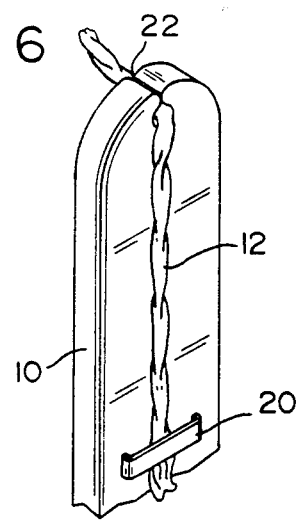
FIG. 6 is an enlarged fragmentary isometric view of the upper terminal end of a handle to which one terminal end of the dental floss loop is secured by means of a slot and a staple.

FIG. 6 is an enlarged fragmentary isometric view of the upper terminal end of one handle of the device of FIG. 5 showing details of the manner of securing one terminal end of one handle of the device of FIG. 5 showing details of the manner of securing one terminal end of the loop of dental floss to the handle 10.

Figure 7:
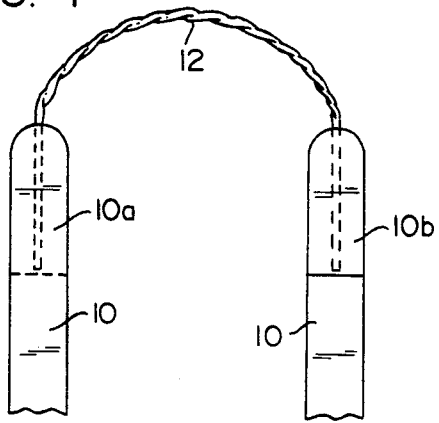
FIG. 7 is a fragmentary plan view of still another modification, wherein the terminal ends of the dental floss loop are fixedly contained between cemented half portions of the upper terminal ends of the handles.
Figure 8:
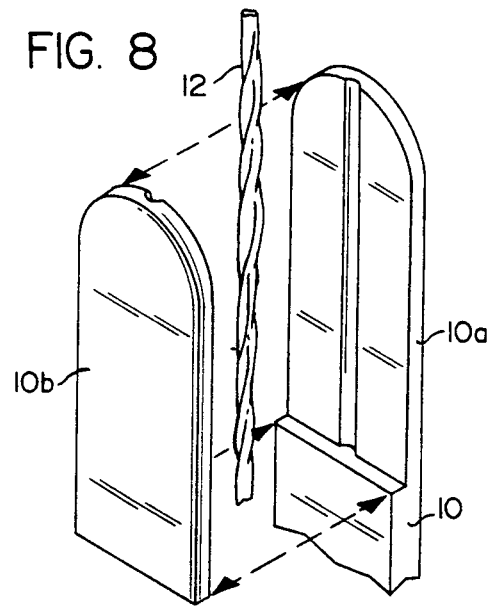
FIG. 8 is an enlarged fragmentary isometric exploded view illustrating the means by which the terminal ends of the dental floss loop are fixedly secured to the upper terminal ends of the handles.

FIGS. 7 and 8 show still another embodiment of the invention; the loop of dental floss 12 being imbedded between and glued to the two halves 10A and 10B of each handle 10.

Figure 9:
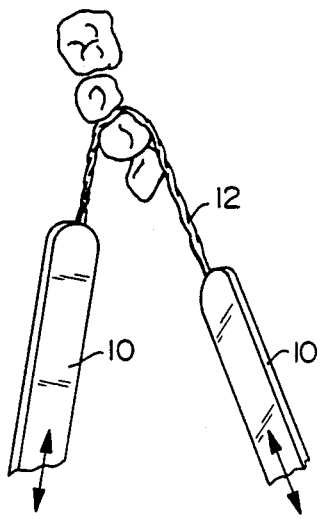
FIGS. 9 and 10 are schematic views showing the preferred method of use of the devices of the invention.
Figure 10:
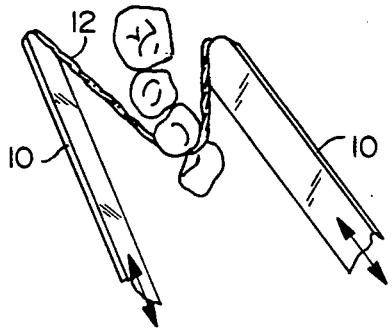

FIGS. 9 and 10 are schematic views showing the preferred method of use of the devices of the invention; the handles 10 being employed to manipulate the loop of dental floss 12 to clean the teeth.

It is essential in the foregoing and other embodiments of the invention, that the length of floss 12 in the loop between the handles 10 be of sufficient length to permit it to be looped around a tooth and worked back and forth laterally as well as vertically over the tooth surface. Such lateral cleaning or polishing is one of the principal advantages of the invention, since it permits the removal of food particles, tartar and plaque at and under the gum line, thus fighting peridontal disease. Therefore, the loop of the dental floss should be at least about 1" long, and preferably, 1½" to 2" long. Such action is shown in FIGS. 9 and 10.

It will be apparent to those skilled in the art that the invention is susceptible to many other embodiments.

What is claimed is:

1. A disposable device for the manipulation of dental floss in cleaning a person's teeth, comprising:
    a pair of separate, substantially elongated handle means in the form of wooden sticks used for frozen confections such as popsicles and ice cream bars, having thin, narrow, flat configuration, and
    a strand of dental floss, said strand of dental floss being from about 1" to about 2" long and fastened at each end to respective inner ends of each of said handle means
whereby the strand of dental floss extends between and connects the inner ends of said pair of handle means, leaving the outer ends of said handle means free,
    said handle means being sufficiently long and stiff to permit leveraged inward, outward and lateral manipulation of said dental floss against all surfaces of a person's teeth when one of the handle means is held in each of the user's hands without inserting of the user's fingers into the person's mouth.

2. In a device for the manipulation of dental floss in cleaning teeth which includes
    a pair of separate elongated handle means and
    a strand or loop of dental floss attached to each of said handle means and extending therebetween,
the improvement which comprises:
    a disposable device in which said pair of separate elongated handle means are thin, narrow, flat popsicle style sticks composed of stiff, inexpensive material, said material being selected from the group consisting of wood, metal, plastic and stiffened paper,
    each of said handle means having
        an upper portion for the attachment of said dental floss and
        a lower portion to be gripped by the user, and
        wherein at least said upper portions of the handle means each include two halves fastened together with one end of the strand of dental floss embedded therebetween.

3. A device of claim 2 wherein the two halves of the handle means are fastened together by an adhesive.

* * * * *